United States Patent
Lu (10) Patent No.: US 9,921,164 B2
(45) Date of Patent: Mar. 20, 2018

(54) SYSTEM AND METHOD FOR MOLECULE SENSING USING EVANESCENT LIGHT COUPLING APPROACH

(71) Applicant: UVic Industry Partnerships Inc., Victoria (CA)

(72) Inventor: Tao Lu, Victoria (CA)

(73) Assignee: UVic Industry Partnerships Inc., Victoria, BC (CA)

( * ) Notice: Subject to any disclaimer, the term of this patent is extended or adjusted under 35 U.S.C. 154(b) by 0 days.

(21) Appl. No.: 15/418,350

(22) Filed: Jan. 27, 2017

(65) Prior Publication Data

US 2017/0328836 A1 Nov. 16, 2017

Related U.S. Application Data

(60) Provisional application No. 62/334,710, filed on May 11, 2016.

(51) Int. Cl.
*G01N 21/65* (2006.01)
*G02B 6/032* (2006.01)
*G02B 6/255* (2006.01)

(52) U.S. Cl.
CPC ........... *G01N 21/658* (2013.01); *G02B 6/032* (2013.01); *G01N 2201/0612* (2013.01); *G01N 2201/08* (2013.01); *G02B 6/2551* (2013.01)

(58) Field of Classification Search
None
See application file for complete search history.

(56) References Cited

U.S. PATENT DOCUMENTS 5,600,433 A * 2/1997 Buttry .................. G01N 21/431
204/452

OTHER PUBLICATIONS

Shin, et al., "All-fiber wavelength- and mode-selective coupler for optical interconnections," *Optics Letters*, 27(21):1884-1886 (Nov. 1, 2002).
Zhang, et al., "Side-channel photonic crystal fiber for surface enhanced Raman scattering sensing," *Sensors and Actuators B: Chemical*, 223:195-201 (Sep. 2015).

* cited by examiner

*Primary Examiner* — Jerry Rahll
(74) *Attorney, Agent, or Firm* — Klarquist Sparkman, LLP (57) ABSTRACT

A system and a method for optical sensing of single molecule or molecules in various concentrations are provided. The optical sensor system comprises a first fiber, a second fiber, a light source and a detection device. The first fiber and the second fiber are fused together to form an optical coupler. The first fiber serves as the passageway for the analyte, while the second fiber serves as the waveguide for the light that will interact with the said analyte. One end of the second fiber is connected to the light source (e.g. laser), and the opposite end is connected to the detection device (e.g. spectrometer). The analyte is introduced into the first fiber through one of its ends, and is allowed to flow through inside the hollow core of the said first fiber. When light is delivered through the input end of the second fiber, the evanescent light is formed in the optical coupler and is allowed to interact with the analyte in the first fiber. One scenario in this analyte-light interaction results in, for example, the generation of Raman emission that is used as the probing signal. The spectrum of the Raman emission is analyzed by the detection device to determine the presence of target molecule.

20 Claims, 11 Drawing Sheets

A. Gold nanorod  B. Bowtie antenna

SYSTEM AND METHOD FOR MOLECULE SENSING USING EVANESCENT LIGHT COUPLING APPROACH

CROSS REFERENCE TO RELATED APPLICATION

This application claims the benefit of U.S. Provisional Application No. 62/334,710, filed on May 11, 2016, which is hereby incorporated by reference in its entirety.

FIELD

The subject matter of this application relates to molecule sensing, and more particularly labelled or label-free optical sensing of single molecule or molecules in wide range of concentrations using evanescent light coupling approach.

BACKGROUND

Many scientific studies and procedures in various fields (e.g. field of medicine) require the detection or sensing of target molecules. For example, early detection of certain diseases requires detection of biomarkers that are present in low level of concentrations during the early stages of the disease. Nucleic acid diagnostics use blotting techniques, polymerase chain reaction and fluorescence methods to undertake the detection of target molecule. However, these techniques usually require samples with high concentration and fluorescence labelling. Labelling has been useful in some cases, but can be challenging in other cases. Although inexpensive, labelling-based sensing methods are generally prone to provide false positives due to the so-called cross-reactivity or interference with other components in the sample under test leading to inaccurate results. Moreover, the surface plasmon resonance (SPR) sensing technique has gained prominence in the sensor world due to its high sensitivity. However, SPR sensor systems in general have a small detection area, which makes the sensing process less efficient and the detection of molecules in low concentration more challenging.

Figure 2:
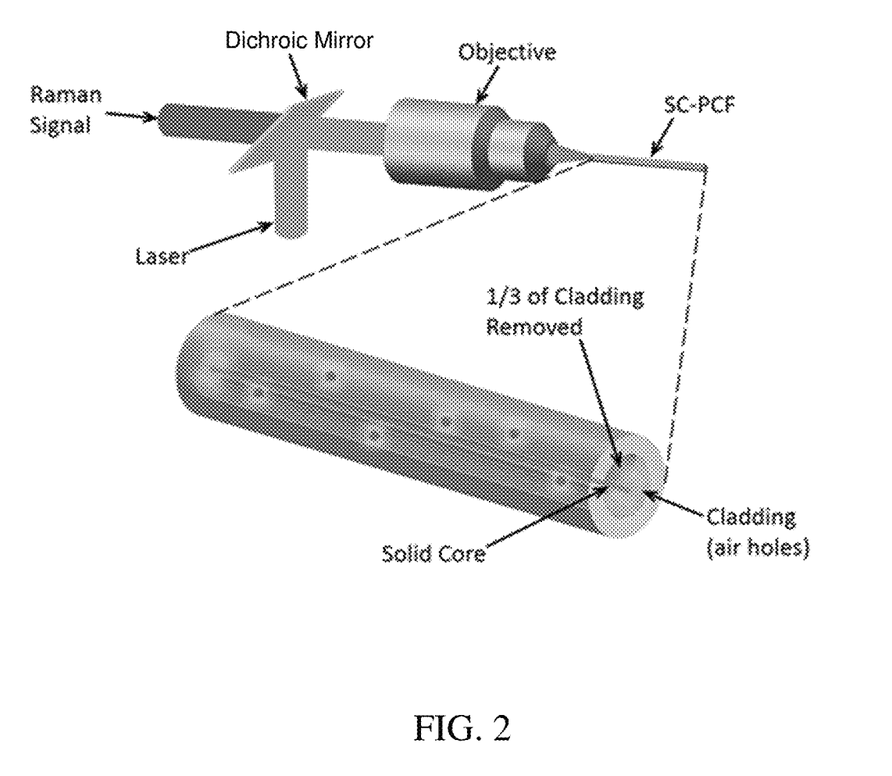
FIG. 2 is the schematic of the work of Nan Zhang, et al.

Further, optical sensing approaches using optical fiber offer a low-cost solution for molecule detection. For example, Nan Zhang, et al., published a technical paper entitled "Side-channel photonic crystal fiber for surface enhanced Raman scattering sensing", that discloses an optical sensor that uses side-channel photonic crystal fiber (SC-PCF) for surface enhanced Raman scattering (SERS) sensing platform (see FIG. 2). The SC-PCF has solid core with air holes cladding arranged in triangular lattice structure, wherein one-third of the said cladding is intentionally removed to facilitate the flow of liquid and the interaction between the liquid sample and the fiber core guided lightwave. The said sensing system requires an objective lens to deliver laser into the solid core of the SC-PCF. This objective lens requires careful alignment with the SC-PCF, making this design of sensing system not fit for applications that require portable sensor and fast analysis. In addition, the said sensing system also uses free space coupling as its approach to couple light into the liquid sample. Free space coupling is quite lossy as evidenced by the result of their experiment wherein transmission loss is estimated to be around −45 dB for fiber length of 1 meter and shorter. This means that the said sensing system will require high power laser system to ensure high sensitivity sensing. Given these limitations associated with current approaches for molecule sensing, there is a need for alternative molecule sensing solution that will address those limitations. Herein, sensing solutions are provided that are low-cost, portable, efficient, and sensitive enough to detect a single molecule and molecules in wide range of concentration (e.g., low concentration to high concentration).

SUMMARY

In some embodiments of the disclosed technology, optical sensor systems for detecting the presence of target molecules include a first fiber that is configured to receive an analyte from at least one of its ends (e.g., input end), a second fiber that can propagate light with acceptable loss, and wherein such second fiber is fused together with the first fiber to form an optical coupler where the evanescent light can propagate from the second fiber to the first fiber to form a probing signal that arises from an interaction between the evanescent light and the analyte and that can be coupled into the second fiber, a light source that is connected to the input end of the second fiber, and is configured to deliver light, and a detection device that is connected to the output end of the second fiber, wherein such detection device is configured to analyze the spectrum of the probing signal associated with the interaction between the evanescent light and the analyte.

Some example methods for detecting the presence of target molecule include delivering light into one end of the second fiber of the optical sensor system, such that a highly focused evanescent light is formed in the fused region and is allowed to propagate from the second fiber to the first fiber, delivering the analyte into the input end of the first fiber of the optical sensor system, allowing the evanescent light to interact with the analyte inside the first fiber, analyzing the spectrum of the probing signal associated with the interaction between the evanescent light and the analyte, and determining the presence of target molecule in the analyte.

In some embodiments, apparatus include an analyte passageway situated to receive an analyte having a measurable optical characteristic, an optical waveguide including an input end separate from the analyte passageway and further including a waveguide portion optically evanescently coupled to a passageway portion of the analyte passageway so as to form an analyte detection region, a light source optically coupled to the input end of the optical waveguide so as to direct a detection beam through the optical waveguide to the analyte detection region to form an analyte response beam associated with the measurable optical characteristic, and an optical detector optically coupled to the optical waveguide so as to receive the analyte response beam from the analyte detection region through the optical waveguide.

In some examples, methods include directing an analyte having a measurable optical characteristic through an analyte passageway so that the analyte is situated in a passageway portion of an analyte detection region that includes an optical evanescent coupling between the passageway portion and a waveguide portion of an optical waveguide that is separate from the analyte passageway, directing an analyte detection beam generated from a light source into an input end of the optical waveguide to the waveguide portion, forming an analyte response beam in the analyte detection region that is associated with the measurable optical characteristic, and directing the analyte response beam through the optical waveguide so as to be received by an optical detector.

The foregoing and other features and advantages of the disclosed technology will become more apparent from the following detailed description, which proceeds with reference to the accompanying figures.

BRIEF DESCRIPTION OF THE DRAWINGS

FIGS. 5A-5B are the schematic showing the cross-section of sample designs of the fiber pair.

FIGS. 6A-6B are the schematic showing the cross-section of sample designs of the first fiber containing single hollow core.

FIGS. 7A-7B are the schematic showing the cross-section of sample designs of the first fiber containing multiple hollow cores.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

In some embodiments of the disclosed technology, through an evanescent light coupling between a regular and a hollow core fiber, molecule targets are spectrally detected in real-time with a low per test cost. In some examples, devices do not require on-site sterilization and are suitable for field tests.

Conventional nucleic acid diagnostic approaches such as blotting techniques, polymerase chain reaction (PCR) and fluorescence methods (e.g. molecular beacon) usually require high concentration samples and/or fluorescence labelling aside from other disadvantages such as bulky in size and high per test cost. Many of them need stringent control on ambient conditions, thus are unsuitable for field tests.

In one example of the disclosed technology, a novel approach using a pair of fibers was used: a hollow fiber and a regular fiber, each 5 cm in length. The pair is fused to an optical coupler such that light can be evanescently coupled between the two fibers. The coupler is fabricated using the same technique to make the regular optical fiber coupler: e.g., using a hydrogen torch to soften the fibers while pulling and fusing them together. The schematic of the device is described in FIG. 1. Here, a standard spectroscopy system with a laser diode, a spectrometer, and supporting electronics can be packaged as a permanent handheld module. The regular fiber of the fused pair is connected between the laser and the spectrometer while the bio samples injected by a syringe flow along the inner core of the hollow fiber. When the light emitting from the laser is delivered to the input end of the regular fiber, it will be evanescently coupled to the hollow core of the hollow fiber, forming a tightly focused "hot spot", or region of high optical intensity, sometimes referred to herein as the analyte detection region of the apparatus. When the bio samples flow through the "hot spot", the light at the spot excites the Raman process from the sample. Analyte located at the hot spot can sometimes be referred to herein as the analyte target. The Raman signal is further evanescently coupled back to the regular fiber and captured by the spectrometer. By analyzing the received Raman spectrum, the bio sample under test can be discerned.

Compared to the conventional methods, device examples can include numerous advantages including high sensitivity. At the fused region, the fibers are tapered. That is, the cross section area of the fiber at the fused region can be more than orders of magnitude smaller than the unfused part. Therefore, the "hot spot" created at the hollow fiber is tightly confined with its cross sectional area close to the diffraction limit. Meanwhile, the light intensity at the hot spot amplifies the input light intensity due to the law of energy conservation. Therefore, Raman emission of samples, which requires high excitation light intensity, can be triggered with a laser diode of typical optical power (e.g., below 10 mW). Further, the light only sees particles within the hot spot while noises arising from off-spot particles are invisible. This significantly improves the signal-to-noise ratio. As mentioned below, the device can be further improved to single molecule resolution by incorporating, e.g. a plasmonic nanorod to break the diffraction limit.

Some device examples can also have a fast sensing time with a low sample concentration/volume. In one-dimensional device examples, target molecules flow across the hot spot. Therefore, a Raman signal is triggered even if the concentration of target molecules is extremely low. On the other hand, the minimum sample volume, which equals to the inner volume of the hollow core, is below 0.5 µL. In addition, the sensing speed is determined by sample flow rate. By injecting the sample at a normal speed, detection as fast as a few seconds can be achieved.

In further examples, analyte samples flow through the inner core of a commercial grade hollow fiber with no contact to ambient environments. Therefore, no sterilization procedure is required for the measurement. This is a unique feature that that makes the device ideal for field test purposes.

In further examples, a low per test cost can be realized due to the low cost per unit length associated with hollow core fiber and the short length of fiber used (e.g., 30 cm, 20 cm, or 5 cm or less per fiber), even assuming the hollow fiber coupler is for one-time-use. With proper rinse/sterilization procedure, the coupler can be reusable, thereby reducing the per test cost even further.

Numerical and experimental data can be used to demonstrate operation of the examples of the disclosed technology. On the numerical side, simulations can show how light propagating within the fiber pair is conducted using commercially available finite element software (e.g., COMSOL) and other numeric tools. Simulation results can include, but not limited to, the size and intensity distribution of the "hot spot", the loss mechanism in our detection system, and noise analysis. From the simulation results, fiber coupling parameters can be adjusted and optimized, such as fiber coupling length, hollow fiber core size at the tapered region, etc., to achieve the tightest hot spot and the maximum signal output. A minimum optical power of the laser diode that triggers a Raman signal detectable by the specified spectrometer can also be identified. Signal spectrum of all test targets can be simulated to compare with experiment results. Experimentally, embodiments are tested with various samples. In some examples, device detection sensitivity can be calibrated with spectroscopy measurement of well calibrated polystyrene micro/nano beads of different sizes. Various bio samples can be tested to confirm device effectiveness.

In some examples, by integrating our sensor on a microfluidic platform, sample volume and minimum concentration may further be reduced. To miniaturize our device and lower the cost, an on-chip spectroscopy system can be constructed by integrating laser diode and the spectrometer with supporting electronics on a silicon-on-insulator (SOI) wafer. A plasmonic nanoantenna, such as gold nanorod, can further break the diffraction limit to reduce "hot spot" size, such as by orders of magnitude, and therefore hotter, leading to single molecule resolution. Plasmonic nanoantenna can be incorporated on the hollow fiber through the state-of-art nanofabrication technologies (see FIG. 1).

Described below are embodiments of the disclosed technology including a system and a method for optical sensing of single molecule or molecules in various concentrations using evanescent light coupling approach. To facilitate a clear description of this disclosed technology, the following terms are used throughout this disclosure. A "molecule" means a particle (e.g. a nanoparticle or a microparticle), a chemical compound (e.g. a biomarker) or a microscopic organism (e.g. virus or bacteria). An "analyte" means a test sample that may contain the target molecule for detection, and can be in the form of a liquid solution, suspension or gas. A "first fiber" means any type of fiber that contains at least one hollow core, such as an analyte passageway, throughout its length where the analyte can flow through. A "second fiber" means any type of optical waveguide or fiber that allows light to propagate throughout its length. A "nanostructure" means a nano-scale physical structure (plasmonic or non-plasmonic type), such as a nanorod or a nanohole, that is used to enhance the intensity of the evanescent light and improve the sensitivity of the hot spot or sensing region. A "probe light" or detection beam means the light coming from the light source that propagates through the second fiber, couples into the first fiber, and interacts with the analyte. An "evanescent light" means the probe light that propagates from the second fiber to the first fiber via evanescent light coupling mechanism. An "optical coupler" means the detection region along the length of the fiber pair where the evanescent light propagates from the second fiber to the first fiber and that can be fused. A "hot spot" means an area in the optical coupler (e.g., fused region, detection region, etc.) wherein the evanescent light is tightly focused, and is generally the area inside the hollow core of the first fiber where a response beam associated with the target molecules is generated. A "light source" means a light-producing device that outputs light for use during sensing, and this includes the light-emitting diode (LED), laser device (e.g. laser diode) and any light source that can be used for sensing applications. A measurable optical characteristic means an optical response associated with the analyte, such as a surface enhanced Raman scattering, though other measurable optical characteristics are possible, including absorption, emission, FT-IR spectroscopic response, variable transmissivity, etc. A "detection device" or "optical detector" means a signal analyzer, such as spectrometer of any type (e.g. Raman spectrometer), a photodetector, or a photomultiplier that is integrated with electronics module for signal processing.

Figure 1:
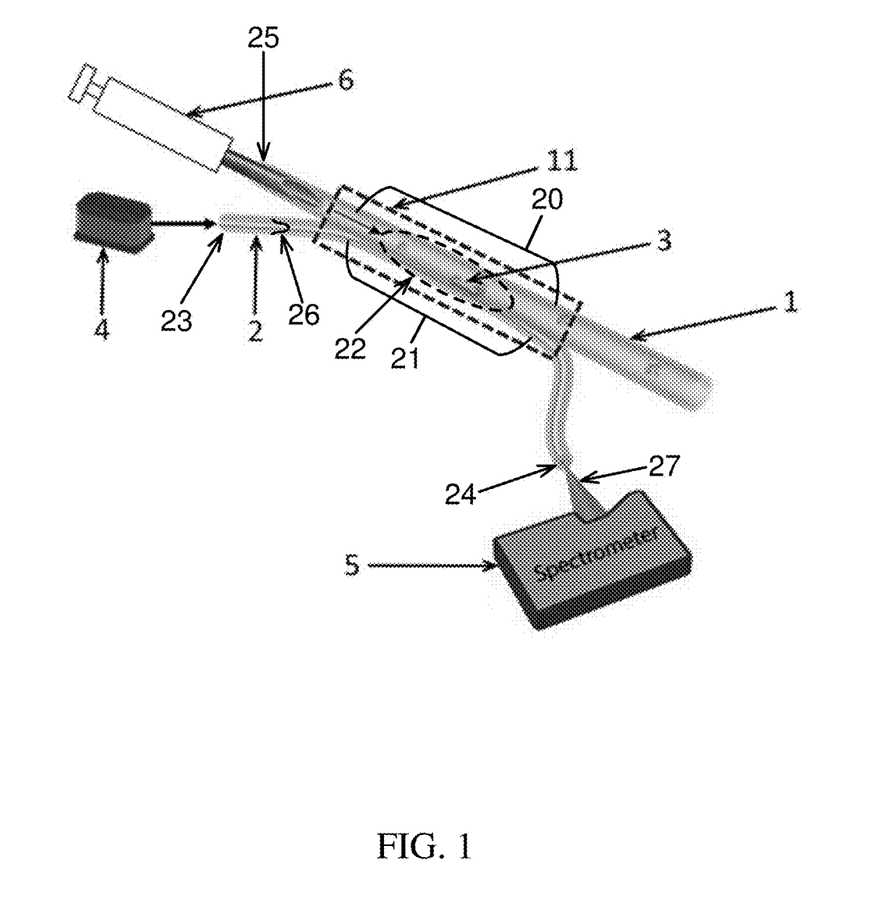
FIG. 1 is the schematics of an embodiment of the disclosed technology that includes an optical sensor using a pair of optical fibers.

In some embodiments, an optical sensor system for molecule sensing comprises a first fiber 1, a second fiber 2, a light source 4, and a detection device 5 (see FIG. 1). A portion 20 of the first fiber 1 and a portion 21 of the second fiber 2 are fused together to form an optical coupler 7, such as a fused fiber coupler, with a corresponding analyte detection region 22, in approximately midway their lengths (see FIG. 3). In typical examples, the first fiber 1 and the second fiber 2 extend alongside each other for predetermined portion of their lengths, and are fused or otherwise brought into close proximity so that the portion 20 and portion 21 can be evanescently coupled. Depending on the application, the optical coupler 7 may be provided with a protection cover 11. One end 23 of the second fiber 2 is connected to a light source 4, and the opposite end 24 is connected to a detection device 5 (see FIG. 4). Using a syringe 6, the analyte 8 is introduced in the input end 25 of the first fiber 1, and is allowed to flow through the hollow core of the said first fiber 1. When the probe light, such as a detection beam 26, from the light source 4 is delivered through the input end 23 of the second fiber 2, which is separate from the input end 25 as it is part of a separate fiber, the said probe light propagates towards the optical coupler 7. In various examples, the detection device 5 can be optically coupled directly or indirectly so that one or more optical elements can be situated between, after, or adjacent the detection device 5 and the detection region 22 of the second fiber 2. For example, one or more optical circulators, optical attenuators, polarization controllers, etc., can be present. In typical examples, the separation between the input ends 23, 25 allows the second fiber 2 to remain substantially analyte free. In the optical coupler 7, an evanescent light 9 is formed and allowed to propagate from the second fiber 2 to the first fiber 1 through evanescent light coupling mechanism. When evanescent light 9 is formed, a hot spot 12 is also created in the optical coupler 7 (see FIG. 4). In general, evanescent coupling can occur when a plurality of optical waves physically overlap. In optical waveguides, close but spaced apart fiber cores can allow an evanescent field that extends into an adjacent core to excite an optical wave in the adjacent core. When the analyte 8 flows through the hot spot region, the tightly focused evanescent light 9 is allowed to interact with the said analyte 8 resulting in the generation of an analyte response beam 27, such as a Raman emission (i.e., Raman signal). This Raman signal is further evanescently coupled back to the second fiber 2 and captured by the detection device 5. In some examples the coupling can occur through scattering or reflection. The spectrum of Raman emission is analyzed in the detection device 5 to determine the presence of the target molecule in the analyte 8. It is also worth mentioning that the proposed optical sensor system is not limited to Raman spectroscopy technique when detecting target molecules. Other spectroscopic techniques can be associated with the response beam, such as absorption, emission, FT-IR spectroscopy, or direct monitoring of analyte-induced transmission/reflection change. For example, it can be used to detect target molecule by monitoring the light transmission change when the analyte flows through the optical coupler 7. In general, when the analyte 8, which typically includes an unknown content of molecules, receives detection light, the analyte 8 produces an optical response that is different depending on what the analyte 8 contains.

Figure 13:
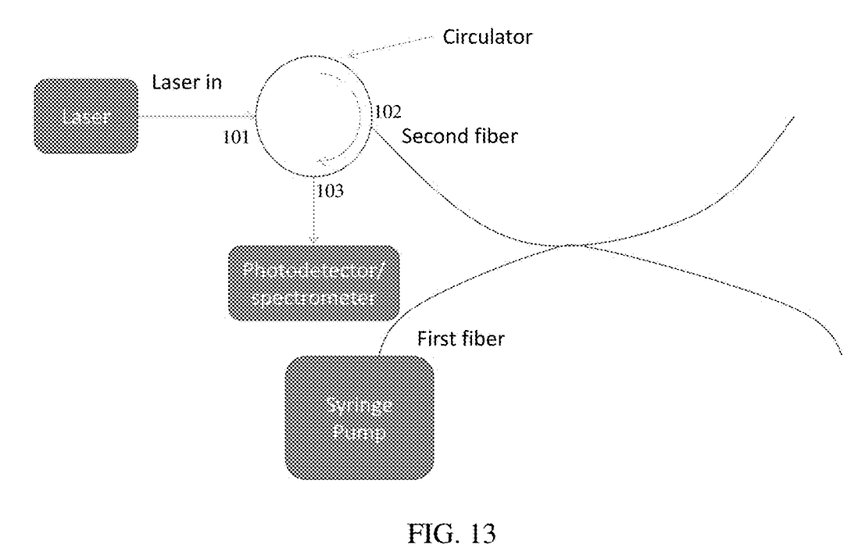
FIG. 13 shows another embodiment that includes a fiber circulator.

In another embodiment, depicted in FIG. 13, a light source and detection device can be at the same end of the second fiber. For example, using a three port circulator, port 101 is connected to the light source, and port 102 is connected to the second fiber, so that the light from port 101 will exit from port 102 to the second fiber, then evanescently coupled to the first fiber, interact with analyte, reflect back to the second fiber through evanescent coupling, the reflected light in the second fiber will exit the input end of the fiber and re-enter port 102 of the circulator and exit at port 103, which can be connected to a detection device. In some embodiments, one or more fiber Bragg gratings or reflective coated fiber ends can be used to ensure that the analyte response beam can propagate out the same end that a detection beam is coupled into.

In one embodiment of the disclosed technology, there is a pair of first fiber 1 and second fiber 2 that consist of photonic crystal fibers. One photonic crystal fiber is employed as waveguide to deliver the light in and out of the sensor, while another photonic crystal fiber is used as passageway to flow the analyte. These photonic crystal fibers are fused together to form an evanescent couple region or optical coupler 7.

Figure 3:
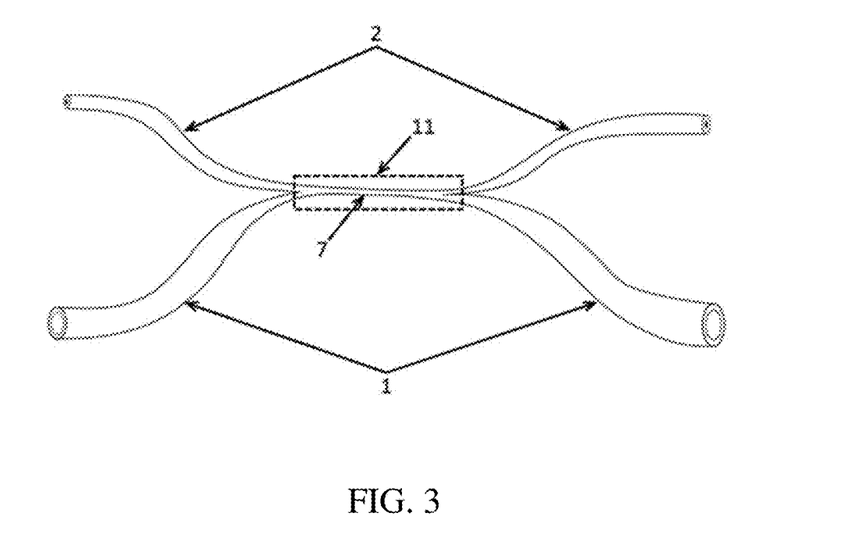
FIG. 3 is the schematic showing the first fiber and the second fiber that are fused together to form an optical coupler. In this schematic, the optical coupler is the fused region that is inside the protection cover, while the unfused region is the portion of the fiber that extends outside the protection cover.
Figure 4:
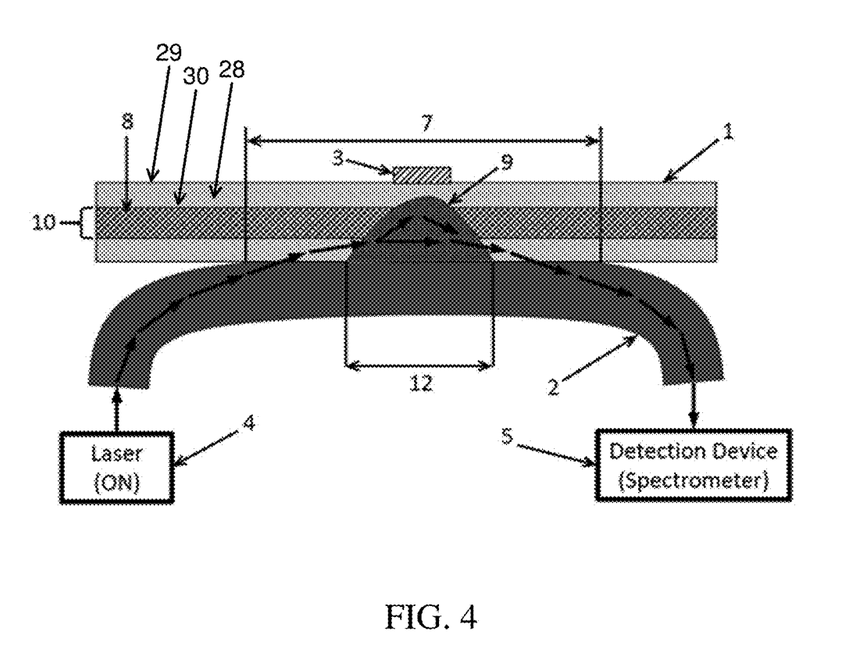
FIG. 4 is the schematic showing the tightly focused evanescent light propagating from the second fiber and interacting with the analyte inside the hollow core of the first fiber.
Figure 5A:
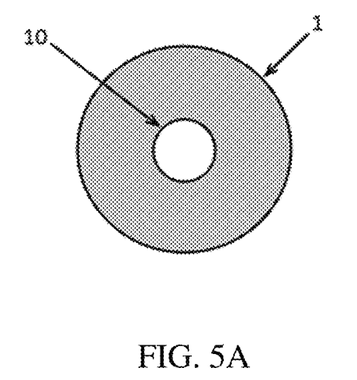
FIG. 5A is the schematic for the first fiber containing a hollow core.
Figure 5B:
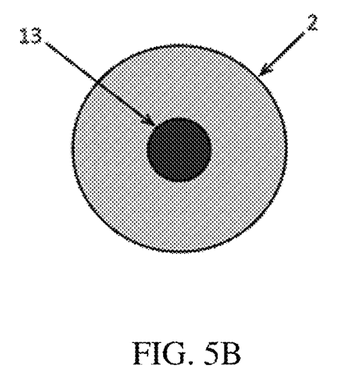
FIG. 5B is the schematic for the second fiber containing a solid core.
Figure 6A:
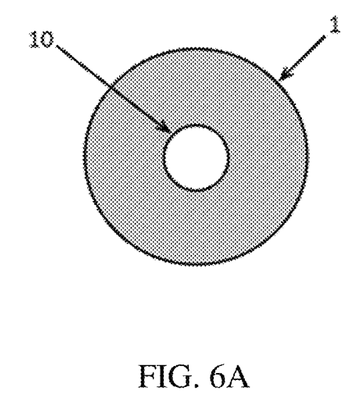
FIG. 6A is the schematic that shows a first fiber containing hollow core of circular cross-section.
Figure 6B:
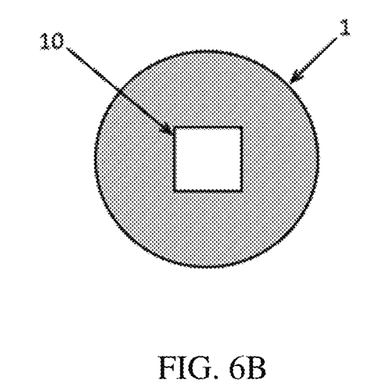
FIG. 6B is the schematic that shows a first fiber containing hollow core of square cross-section.
Figures 7A, 7B:
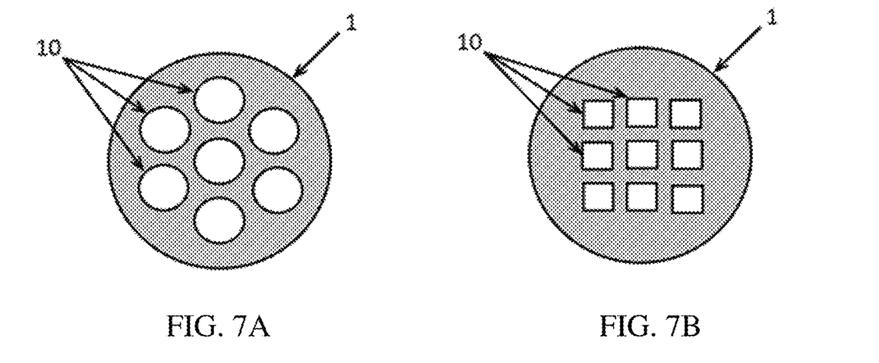
FIG. 7A is the schematic that shows a first fiber containing hollow cores of circular cross-section.
FIG. 7B is the schematic that shows a first fiber containing hollow cores of square cross-section.

In another embodiment of the disclosed technology, there is a first fiber 1 that is a microstructured optical fiber containing at least one hollow core 10 throughout its length (see FIGS. 3 and 5A-5B). The hollow core 10 of first fiber 1 serves as the passageway for the analyte 8. The first fiber 1 is an elongated body that includes a solid cladding 28 having an exterior surface 29 and an interior surface 30. In the illustrated embodiment the cladding 28 is a tubular wall having an interior surface 30 that defines the hollow core 10. In some examples, the solid cladding 28 extends from the interior surface 30 to the exterior surface 29. One end of the first fiber is used as input end where the analyte 8 is introduced by any viable means such as injection through a syringe. In short, the first fiber 1 is typically a hollow core fiber.

In another embodiment of the disclosed technology, there is a first fiber 1 containing at least one hollow core 10 with cross-section of any practical shape. For example, the cross-section of hollow core 10 can be, but not limited to, circular or square in shape (see FIGS. 6A, 6B, 7A, and 7B).

In yet another embodiment of the disclosed technology, there is a second fiber 2 that is fused together with a first fiber 1 in the region approximately midway their lengths so as to form the optical coupler 7 as a fused fiber coupler. Fusing these two fibers can be accomplished using a hydrogen torch to soften the fibers while pulling. Unlike the first fiber 1, the second fiber 2 is any kind of optical fiber that allows the transmission of probe light through its length. It serves as the waveguide to deliver the probe light from the light source 4 towards the optical coupler 7 and to deliver the Raman signal from the hot spot 12 to the detection device 5 (see FIG. 4). In typical examples, the second fiber 2 is an optical waveguide that propagates light with low loss, such as less than 0.5 db/m, 0.25 db/m, 0.1 db/m, etc. This second fiber 2 can be in the form of but not limited to photonic crystal fiber, single-mode fiber, multi-mode fiber, hollow core fiber, or solid core fiber. However, it is possible that an optical fiber with solid core 13 maybe preferred over an optical fiber with hollow core 10 on certain applications.

In yet another embodiment of the disclosed technology, there is a pair of first fiber 1 and second fiber 2 that are fused together such that the cross-sectional area of both fibers is tapered towards the region where the optical coupler 7 is located. As shown in FIG. 3, the cross-sectional area of the fiber at the location of the optical coupler 7 (e.g., fused region) is significantly smaller than that of the unfused part (e.g., outside the location of optical coupler 7). Due to fiber tapering, the hot spot 12 is tightly confined within a cross-sectional area that is close to the diffraction limit. Due to the law of energy conservation, the light intensity at the hot spot 12 is an amplified version of the input light intensity (e.g., intensity of probe light coming from the light source 4). Therefore, the Raman emission of analyte, which requires high excitation light intensity, can be easily triggered even by a light source with low optical power (e.g. a laser diode). In short, the tapering of the fibers significantly improves the sensitivity performance of the proposed optical sensor system. In typical examples, the proximity of the two fiber cores in the fused region is on the order of a few wavelengths.

In yet another embodiment of the disclosed technology, there is a light source 4 that delivers high intensity light through the length of the second fiber 2. For cost-effectiveness, a laser diode is preferred to be used as the light source 4. However, to maximize the sensitivity performance of the proposed optical sensor system, high power laser systems can also be used as the light source 4, including pulsed laser systems.

In yet another embodiment of the disclosed technology, there is a detection device 5 that is in the form of but not limited to a spectrometer, a photodetector, or a photomultiplier that is integrated with electronics module for signal processing. When used as the detection device 5, the spectrometer can be of any type which include Raman spectrometer. A Raman spectrometer system integrated with an electronics module for processing a Raman signal can be used to determine the presence of target molecule. Processing the Raman signal includes capturing and analyzing the spectrum of the Raman signal associated with the interaction between the evanescent light 9 and the analyte 8.

Figure 14:
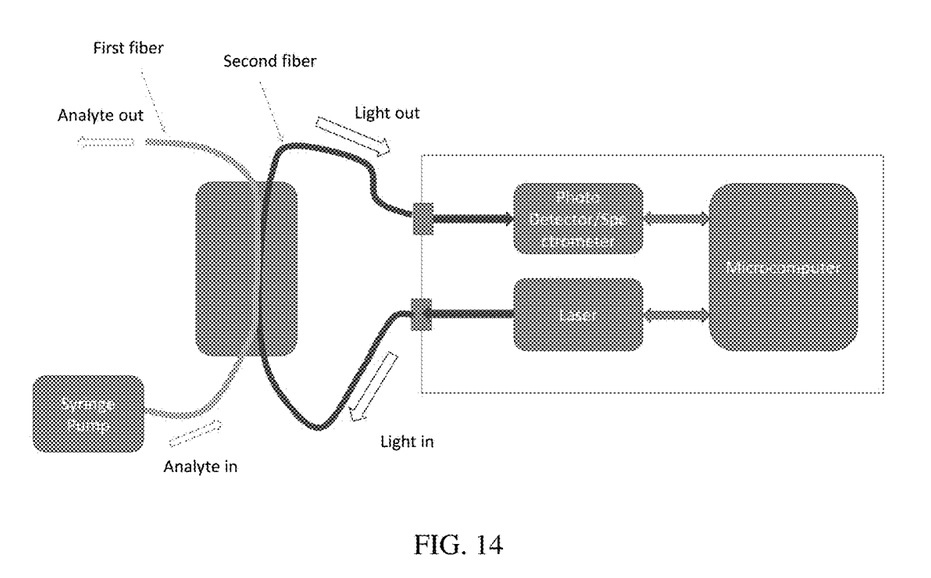
FIG. 14 shows a schematic of a handheld device.
Figure 15:
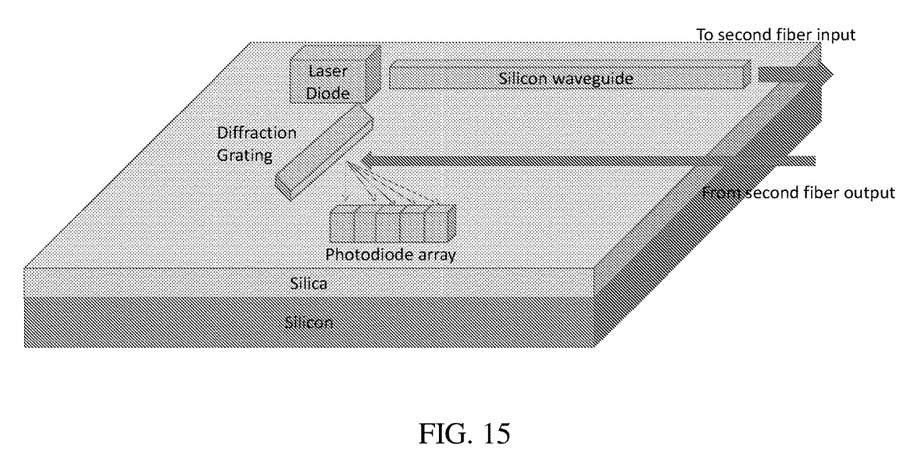
FIG. 15 is a perspective illustration of a silicon-on-insulator wafer embodiment.
Figure 18:
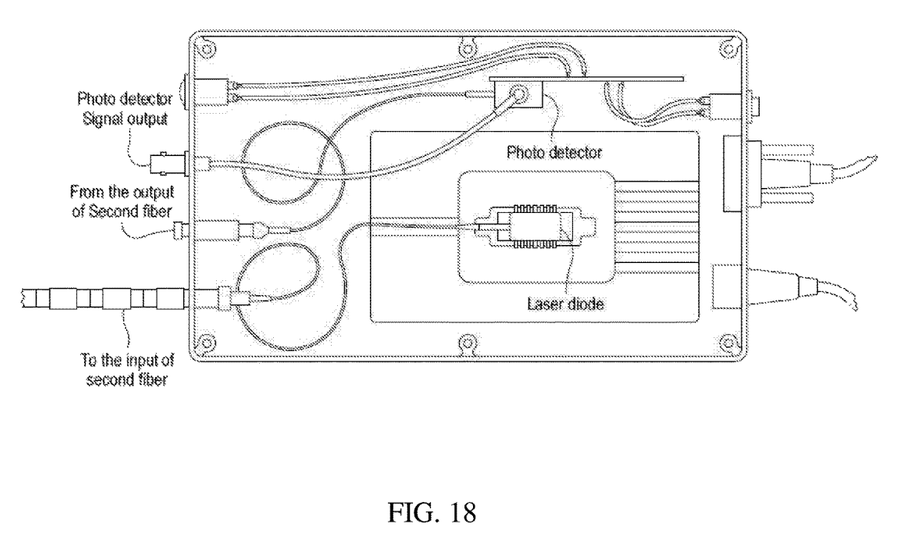
FIG. 18 is an image of a portable sensing device.

In yet another embodiment of the disclosed technology, there is an assembly of the light source 4 (e.g. laser diode) and the detection device 5 (e.g. spectrometer) with supporting electronics in a housing to form a portable handheld module, such as the one shown in FIG. 14, and also in FIG. 18. This portable handheld module gathers and analyzes relevant measurements to determine the presence of target molecule in the analyte 8. To minimize the manufacturing cost and miniaturize the optical sensor system, this whole assembly of the light source 4 and the detection device 5 can be constructed on a silicon-on-insulator wafer to form an on-chip spectroscopy system, as shown in one example in FIG. 15.

Figure 16:
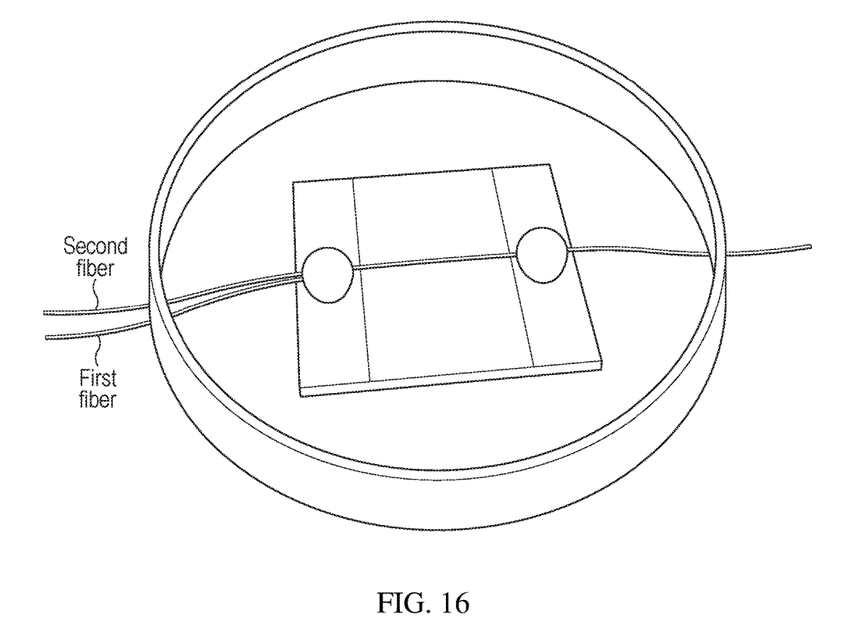
FIG. 16 is an image of a biochip prototype.

In yet another embodiment of the disclosed technology, there is a pair of first fiber 1 and second fiber 2 that are assembled to form a biochip (e.g., a test chip), as shown in one example in FIG. 16. The analyte is delivered into this biochip through syringe injection. This biochip is designed for insertion into the aforementioned portable handheld module where relevant measurements are gathered and analyzed. Thus, the analyte detection region on the biochip is removably optically couplable with the light source 4 and the detection device 5 which are situated in an analyte analyzer housing alongside other components, such as various electronics supporting the detection device 5.

Figure 17:
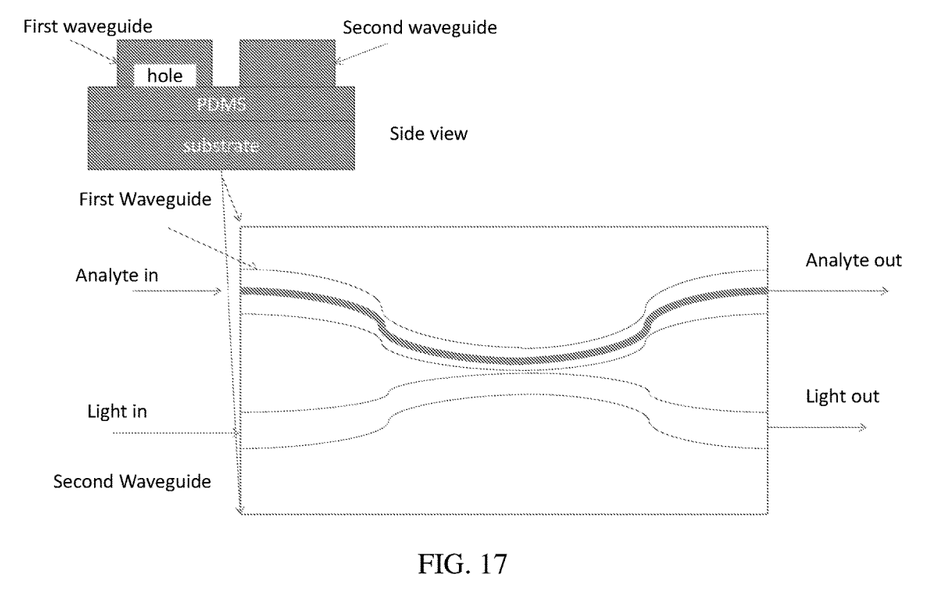
FIG. 17 is a schematic of a microfluidic embodiment.

In yet another embodiment of the disclosed technology, there is an optical sensor system that employs microfluidic design, as shown in one example in FIG. 17. A solid core waveguide and a hollow core waveguide are coupled into a directional optical coupler, wherein these three physical features are implemented on a microfluidic chip. The analyte flows through the hollow core waveguide, while the probe light is delivered in and out of the evanescent coupling region via the solid core waveguide.

Figure 9:
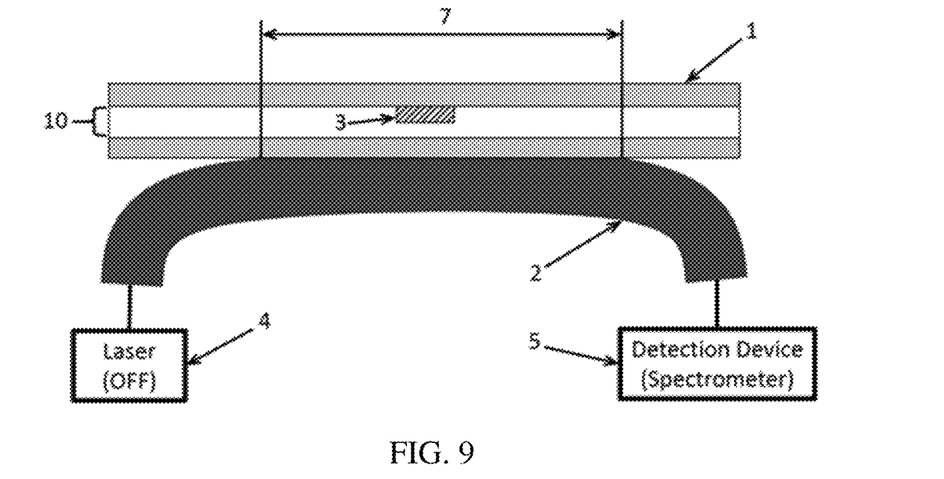
FIG. 9 is the schematic showing the magnified cross-sectional view of the optical coupler wherein the nano structure is on the hollow core surface of the first fiber. In this setup, no analyte has been introduced into the first fiber, and no light has been delivered into the second fiber.
Figure 10:
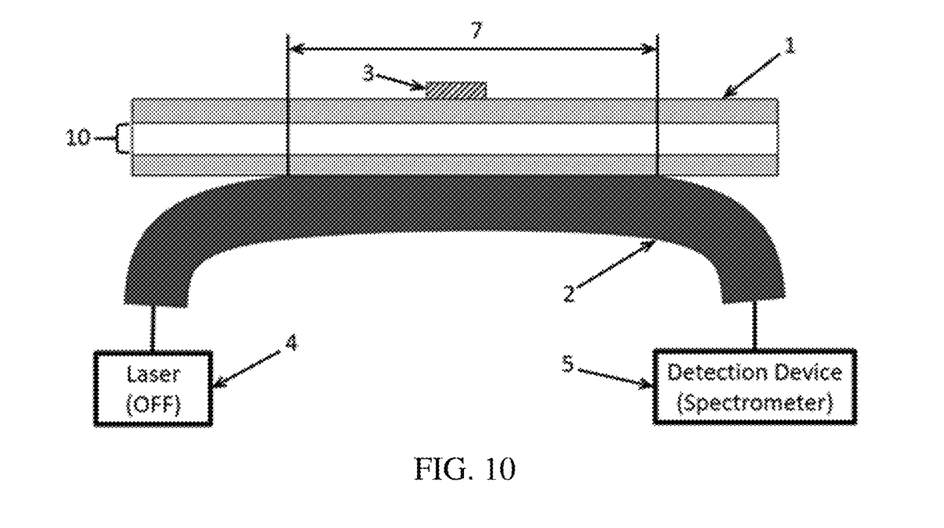
FIG. 10 is the schematic showing the magnified cross-sectional view of the optical coupler wherein the nanostructure is on the exterior surface of the first fiber. In this setup, no analyte has been introduced into the first fiber, and no light has been delivered into the second fiber.
Figure 11:
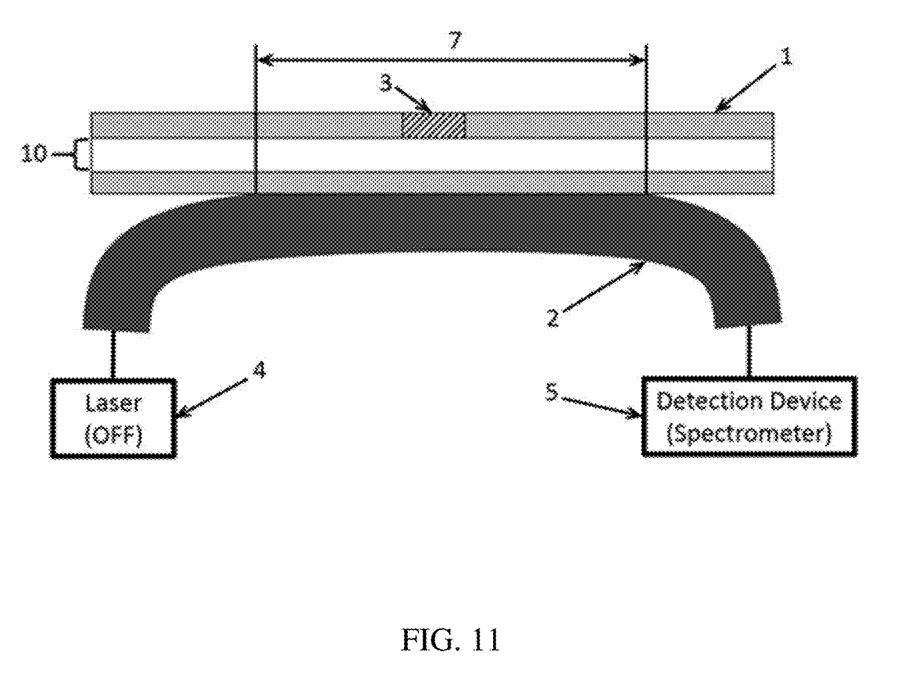
FIG. 11 is the schematic showing the magnified cross-sectional view of the optical coupler wherein the nanostructure is a nanohole or through-hole feature on the first fiber. In this setup, no analyte has been introduced into the first fiber, and no light has been delivered into the second fiber.

In yet another embodiment of the disclosed technology, there is a nanostructure 3 that is strategically placed in the optical coupler 7 close to the proximity of the first fiber 1 to further minimize the volume of the hot spot. This nanostructure 3 serves as a nanoantenna that focuses the evanescent light 9 to form a tightly focused hot spot 12. Serving as a nanoantenna, the nanostructure 3 can facilitate to break the diffraction limit to make the hot spot orders of magnitude smaller than the cross-section of the hollow core, such as a fraction of a wavelength of the beams or on the order tens of $nm^2$, leading to detection of particles as small as single protein molecule (e.g., with a concentration as small as a single particle in the analyte sample). However, it should be noted that the use of the nanostructure 3 in the proposed optical sensor system is optional only depending on specific applications (e.g. cases involving single molecule detection). Moreover, the nanostructure 3 can be incorporated on the first fiber 1 using nanofabrication techniques. Nanostructure 3 can be deposited on the exterior surface of first fiber 1 or on the hollow core surface of first fiber 1 (e.g., interior of first fiber 1) as shown in FIGS. 9 and 10. Nanostructure 3 can also be implemented as a nanohole feature on the first fiber 1 as shown in FIG. 11.

Figure 8A:
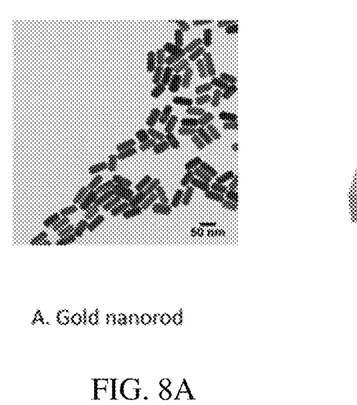
FIGS. 8A and 8B shows examples of possible forms of the nanostructure.
Figure 8B:
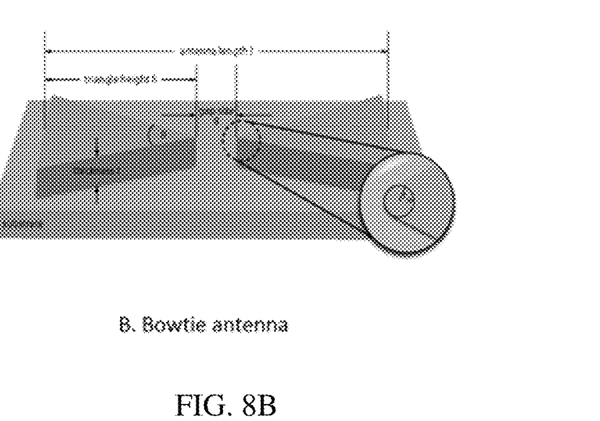

In yet another embodiment of the disclosed technology, the nanostructure 3 can be either plasmonic or non-plasmonic type. Metallic nanostructures with tailored shapes, such as the gold nanorod, are examples of nanostructure 3 serving as plasmonic nanoantenna. In short, the nanostructure 3 is a nanoantenna of any form such as a nanorod, nanosphere, nanohole and bowtie antenna (see FIGS. 8A and 8B).

Moreover, example methods for optical sensing of single molecule or molecules in various concentrations using the aforementioned optical sensor system can include delivering high intensity probe light from the light source 4 into one input end of the second fiber 2 of the optical sensor system, such that a highly focused evanescent light 9 is formed in the optical coupler 7 and is allowed to propagate from the second fiber 2 to the first fiber 1 through evanescent light coupling mechanism, delivering the analyte 8 into the input end of the first fiber 1 of the optical sensor system, allowing the evanescent light 9 to interact with the analyte 8 that flows inside the hollow core 10 of the first fiber 1, analyzing the spectrum associated with the Raman signal (i.e., Raman emission) generated from the interaction between the evanescent light 9 and the analyte 8, and determining the presence of the target molecule in analyte 8 upon analyzing the Raman signal using the detection device 5.

Figure 12:
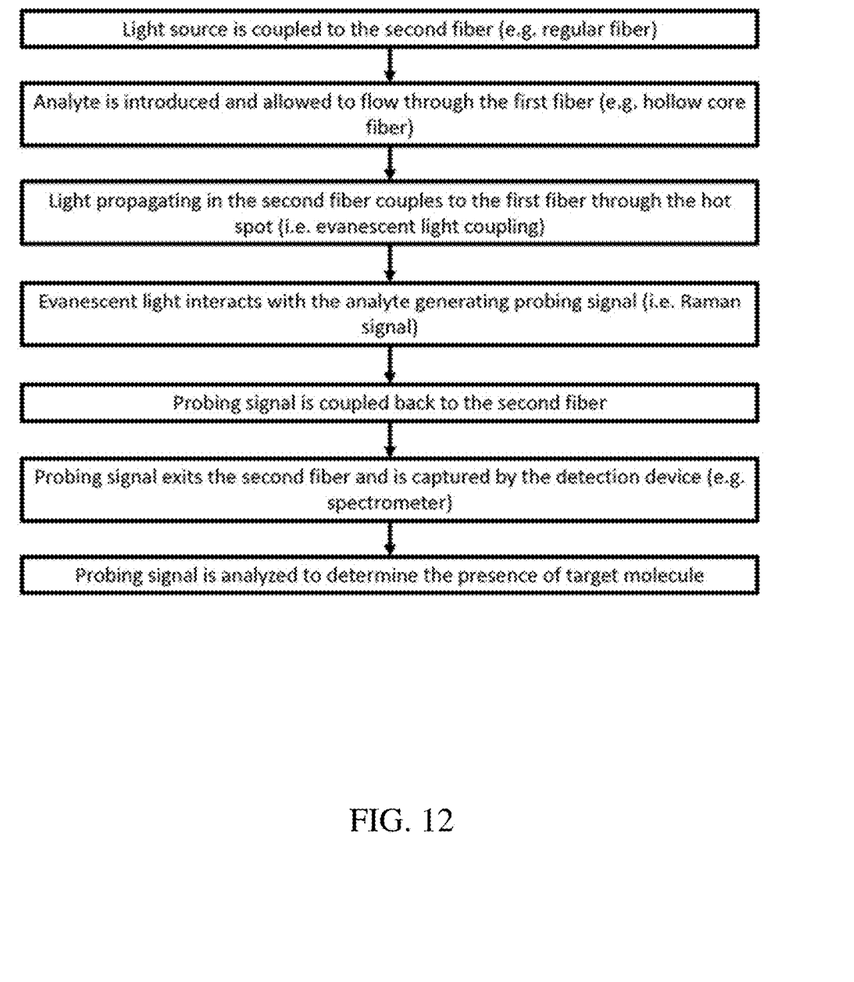
FIG. 12 is the flowchart showing the steps to analyze the analyte using the disclosed technology (optical sensor system).

As the evanescent light 9 interacts with the analyte 8, a Raman signal (i.e. Raman emission) is generated. This Raman signal corresponds to a probing signal, or response beam, used to detect the target molecule. Such probing signal is coupled back to the second fiber 2 and exits in the output end of the said second fiber 2 (or the input end in some examples, together with the input of the light source 4) where the detection device 5 is connected (see FIGS. 4 and 12). The probing signal is captured and its spectrum is analyzed by the detection device 5 (e.g., Raman spectrometer). Upon analysis of the spectrum associated with the analyte 8, a database of Raman spectra of known substances is searched for possible match. If a match is found, the detection of target molecule is confirmed. To maximize the detection confidence, a particle classification mechanism such as a machine learning-based logistic regression or a more sophisticated deep learning approach can be used.

In one aspect of the disclosed technology, there is an optical sensing method wherein the probe light propagating in the second fiber 2 is coupled to the first fiber 1 using evanescent light coupling approach. This coupling approach is in contrast with the work of Nan Zhang, et al. wherein free space coupling of light to a photonic crystal fiber is used (see FIG. 2). In free space coupling approach, precise alignment of the light source in front of the fiber is required. Any misalignment can contribute to significant signal loss. To ensure precise alignment, an objective lens system is typically used to couple the light source and the fiber. The use of the objective lens system increases the overall cost of the sensor system, as well as adds complexity in the operation making it practically unfit for a portable version of the sensor system. There is also a substantial amount of absorption loss of the light in the liquid as the light travels through the length of the fiber. This absorption loss is proportional to the length of the fiber. More importantly, the light shines all liquid (e.g., analyte) in the fiber so all molecules will be probed, making the detection of single molecule or molecules in low concentration more difficult. On the other hand, the evanescent light coupling approach used in embodiments of the disclosed technology herein, makes the disclosed technology more cost-effective and suitable for applications needing portable sensor system. The pair of fibers are relatively inexpensive compared to the objective lens system. According to some examples herein, because probing can be done on a tightly focused hot spot, only a small section of the flowing analyte is probed so single molecule detection is feasible.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope and spirit of the appended claims.

I claim:

1. An apparatus, comprising:
   a fiber defining an analyte passageway situated to receive an analyte having a measurable optical characteristic;
   an optical waveguide including an input end separate from the analyte passageway and further including a waveguide portion optically evanescently coupled to a passageway portion of the analyte passageway so as to form an analyte detection region;
   a light source optically coupled to the input end of the optical waveguide so as to direct a detection beam through the optical waveguide to the analyte detection region to form an analyte response beam associated with the measurable optical characteristic; and
   an optical detector optically coupled to the optical waveguide so as to receive the analyte response beam from the analyte detection region through the optical waveguide;
   wherein the analyte detection region comprises a fused fiber coupler.

2. The apparatus of claim 1, wherein the fiber is a hollow fiber having a hollow interior defining the analyte passageway and the hollow fiber includes a first end situated to receive the analyte, and wherein the optical waveguide is an optical fiber.

3. The apparatus of claim 2, wherein the optical detector is optically coupled to a second end of the optical fiber that is opposite the input end.

4. The apparatus of claim 2, wherein the hollow fiber further includes a second end opposite the first end and situated to drain the analyte from the analyte passageway.

5. The apparatus of claim 1, wherein the analyte passageway and the optical waveguide are tapered so as to reduce a diameter of at least one of a core of the optical detection fiber and analyte passageway in the fused fiber coupler so as to increase a signal strength of the analyte response beam associated with a surface enhanced Raman scattering (SERS).

6. An apparatus, comprising:
   a fiber defining an analyte passageway situated to receive an analyte having a measurable optical characteristic;
   an optical waveguide including an input end separate from the analyte passageway and further including a waveguide portion optically evanescently coupled to a passageway portion of the analyte passageway so as to form an analyte detection region;
   a light source optically coupled to the input end of the optical waveguide so as to direct a detection beam through the optical waveguide to the analyte detection region to form an analyte response beam associated with the measurable optical characteristic;
   an optical detector optically coupled to the optical waveguide so as to receive the analyte response beam from the analyte detection region through the optical waveguide;
   an analyte analyzer housing situated to house the light source and the optical detector; and
   a removable biochip couplable to the analyte analyzer housing and that includes the analyte detection region and the analyte passageway so that the waveguide portion of the analyte detection region is removably optically couplable with the light source and the optical detector.

7. The apparatus of claim 6, further comprising a syringe operable to inject the analyte into the analyte passageway.

8. The apparatus of claim 1, wherein the light source comprises one or more fiber-coupled laser diodes optically coupled to the optical waveguide input end.

9. The apparatus of claim 8, wherein the one or more fiber-coupled laser diodes have an output power that corresponds to a signal strength of the analyte response beam that is associated with a concentration of the analyte.

10. An apparatus, comprising:
    a fiber defining an analyte passageway situated to receive an analyte having a measurable optical characteristic;
    an optical waveguide including an input end separate from the analyte passageway and further including a waveguide portion optically evanescently coupled to a passageway portion of the analyte passageway so as to form an analyte detection region;
    a light source optically coupled to the input end of the optical waveguide so as to direct a detection beam through the optical waveguide to the analyte detection region to form an analyte response beam associated with the measurable optical characteristic; and
    an optical detector optically coupled to the optical waveguide so as to receive the analyte response beam from the analyte detection region through the optical waveguide;
    wherein the analyte detection portion includes at least one nanostructure situated to locally increase an intensity of the detection beam in the analyte detection portion so as to increase a signal strength of the analyte response beam.

11. The apparatus of claim 10, wherein the fiber has an exterior surface and an interior surface and includes a solid cladding extending between the exterior surface and the interior surface, wherein the interior surface defines the analyte passageway that is situated to receive the analyte, and wherein the at least one nanostructure is situated on one or more of the exterior surface and the interior surface.

12. The apparatus of claim 10, wherein the at least one nanostructure includes one or more of a plasmonic or non-plasmonic nanoantenna, nanohole, nanorod, and nanosphere.

13. The apparatus of claim 12, wherein the at least one nanostructure includes a nano-bowtie antenna.

14. The apparatus of claim 1, wherein the analyte detection portion has a length of less than or equal to 5 cm.

15. The apparatus of claim 1, further comprising a signal analyzer coupled to the optical detector so as to receive an optical detector signal corresponding to the measurable optical characteristic.

16. An apparatus, comprising:
a fiber defining an analyte passageway situated to receive an analyte having a measurable optical characteristic;
an optical waveguide including an input end separate from the analyte passageway and further including a waveguide portion optically evanescently coupled to a passageway portion of the analyte passageway so as to form an analyte detection region;
a light source optically coupled to the input end of the optical waveguide so as to direct a detection beam through the optical waveguide to the analyte detection region to form an analyte response beam associated with the measurable optical characteristic; and
an optical detector optically coupled to the optical waveguide so as to receive the analyte response beam from the analyte detection region through the optical waveguide;
wherein the measurable optical characteristic is a surface enhanced Raman scattering (SERS) response.

17. An apparatus, comprising:
a fiber defining an analyte passageway situated to receive an analyte having a measurable optical characteristic;
an optical waveguide including an input end separate from the analyte passageway and further including a waveguide portion optically evanescently coupled to a passageway portion of the analyte passageway so as to form an analyte detection region;
a light source optically coupled to the input end of the optical waveguide so as to direct a detection beam through the optical waveguide to the analyte detection region to form an analyte response beam associated with the measurable optical characteristic; and
an optical detector optically coupled to the optical waveguide so as to receive the analyte response beam from the analyte detection region through the optical waveguide;
wherein the analyte response beam is a single molecule detection signal of a single molecule in the analyte.

18. A method, comprising:
directing an analyte having a measurable optical characteristic through an analyte passageway so that the analyte is situated in a passageway portion of an analyte detection region that includes an optical evanescent coupling between the passageway portion and a waveguide portion of an optical waveguide that is separate from the analyte passageway;
directing an analyte detection beam generated from a light source into an input end of the optical waveguide and to the waveguide portion thereby causing the formation of an analyte response beam that is associated with the measurable optical characteristic;
directing the analyte response beam through the optical waveguide to an optical detector; and
analyzing the analyte response beam with a spectrometer coupled to the optical detector so as to determine a surface enhanced Raman scattering (SERS) response of the analyte.

19. An apparatus, comprising:
a fiber defining an analyte passageway situated to receive an analyte having a measurable optical characteristic;
an optical waveguide including an input end separate from the analyte passageway and further including a waveguide portion arranged parallel to the analyte passageway and optically evanescently coupled to a passageway portion of the analyte passageway through a side of the analyte passageway so as to form an analyte detection region;
a light source optically coupled to the input end of the optical waveguide so as to direct a detection beam through the optical waveguide to the analyte detection region to form an analyte response beam associated with the measurable optical characteristic; and
an optical detector optically coupled to the optical waveguide so as to receive the analyte response beam from the analyte detection region through the optical waveguide.

20. An apparatus, comprising:
a fiber defining an analyte passageway situated to receive an analyte having a measurable optical characteristic;
an optical waveguide including an input end separate from the analyte passageway and further including a waveguide portion optically evanescently coupled to a passageway portion of the analyte passageway so as to form an analyte detection region;
a light source optically coupled to the input end of the optical waveguide so as to direct a detection beam through the optical waveguide to the analyte detection region to form an analyte response beam associated with the measurable optical characteristic with light evanescently coupled back into the optical waveguide from the analyte passageway; and
an optical detector optically coupled to the optical waveguide so as to receive the analyte response beam from the analyte detection region through the optical waveguide.

* * * * *